United States Patent [19]

Berg

[11] Patent Number: 5,334,253

[45] Date of Patent: Aug. 2, 1994

[54] SOLUTION OF CERTAIN FIVE AND SIX CARBON ATOM CARBOHYDRATES

[75] Inventor: Lloyd Berg, 1314 S. Third Ave., Bozeman, Mont. 59715

[73] Assignee: Lloyd Berg, Bozeman, Mont.

[21] Appl. No.: 611,718

[22] Filed: Nov. 13, 1990

[51] Int. Cl.$^5$ .................... C13F 3/00; C08L 5/00; C07H 1/00
[52] U.S. Cl. .................... 127/63; 106/162; 536/1.11; 536/124; 568/868
[58] Field of Search .......... 106/162; 127/63; 536/1.11, 124; 568/868

[56] References Cited

U.S. PATENT DOCUMENTS

| | | | |
|---|---|---|---|
| 3,290,263 | 12/1966 | Smythe et al. | 536/1.1 |
| 3,420,931 | 1/1969 | Daum et al. | 106/162 |
| 4,029,878 | 6/1977 | Kruse | 536/1.11 |
| 5,089,307 | 2/1992 | Ninomiya et al. | 106/162 |

OTHER PUBLICATIONS

Libby, Robert A. "Direct Starch Analysis Using DMSO Solubilization and Glucoaylase" May 1970, pp. 273–281.

*CRC Handbook of Chemistry and Physics*, R. C. Weast, ed. 70th edition, pp. C-38, C-287, and C-344.

"*The Merck Index: An Encyclopedia of Chemicals and Drugs*", 9th ed., M. Windholz, ed., pp. 1126–1127.

*Primary Examiner*—Paul Lieberman
*Assistant Examiner*—P. L. Hailey

[57] ABSTRACT

A method for dissolving sorbitol, xylitol, mannitol, glucose and gluconic acid. Effective agents are dimethylsulfoxide, dimethylformamide or dimethylacetamide.

1 Claim, No Drawings

SOLUTION OF CERTAIN FIVE AND SIX CARBON ATOM CARBOHYDRATES

FIELD OF THE INVENTION

This invention relates to a method for catalytic hydrocracking of some five and six carbon atom carbohydrates using certain solvents to dissolve the carbohydrates.

DESCRIPTION OF THE PRIOR ART

Many of the carbohydrates containing five or six carbon atoms are solid compounds of the sugar family. These compounds are also poly hydroxy compounds. When they are subjected to a cracking catalyst in the presence of hydrogen, they break up into fragments of fewer carbon atoms. Since these carbohydrates are poly hydroxy compunds, the fragments also contain hydroxy groups. Typically, a reaction product will comprise a mixture of alcohols, glycols and polyols. An example of a typical mixture obtained from an aqueous solution of sorbitol over a nickel catalyst is shown in Table 1.

TABLE 1

Polyols Produced By Hydrocracking Of Sorbitol

| Compound | Weight Percent | Boiling Point, °C. |
| --- | --- | --- |
| 2,3-Butanediol | 3.5 | 182 |
| Proylene lycol | 16.5 | 187 |
| 1,2-Butanediol | 2.0 | 192 |
| Ethylene glycol | 25.2 | 198 |
| 1,3-Butanediol | 2.7 | 206 |
| 2,3-Hexanediol | — | 206 |
| 1,2-Pentanediol | — | 210 |
| 1,4-Pentanediol | — | 220 |
| 1,4-Butanediol | 2.1 | 230 |
| 1,5-Pentanediol | 0.1 | 242 |
| Diethylene glycol | 2.2 | 245 |
| 1,6-Hexanediol | — | 250 |
| Triethylene glycol | 2.1 | 285 |
| Glycerine | 38.8 | 290 |
| 1,2,4-Butanetriol | 4.8 | 190/18 mm. |
|  | 100.0 |  |

The carbohydrates must be dissolved in a liquid to contact the catalyst. The usual method is by the use of water. The difficulty encountered with this procedure is that when the carbohydrate is dissolved in water, the aqueous mixture is acidic. With sorbitol, the aqueous mixture has a pH of 3.5. Many of the best hydrocracking catalysts are adversely affected by acids and deteriorate so rapidly that their use is not commercially viable.

OBJECTIVE OF THE INVENTION

It is the object of this invention to provide a method of putting carbohydrates in a liquid phase which is closely neutral with respect to acidity or basicity.

SUMMARY OF THE INVENTION

The objects of this invention are provided by a method for converting carbohydrates into a neutral liquid phase by the use of certain specific organic compounds as the solvent.

DETAILED DESCRIPTION OF THE INVENTION

I have discovered that certain organic compounds will dissolve specific carbohydrates and give a dissolved single liquid phase possessing a pH close to 7, that is, neutral with respect to acidity-basicity.

The compounds which are effective solvents for sorbitol are 1,2,6-hexanetriol, 1,2,4-butanetriol, glycerine, tetraethylene glycol, dimethylsulfoxide, dimethylformamide, dimethylacetamide, diethylene glycol ethyl ether, ethylene glycol ethyl ether and propylene glycol methyl ether.

The compounds which are effective solvents for xylitol are 1,2,6-hexanetriol, 1,2,4-butanetriol, glycerine, tetraethylene glycol, dimethylsulfoxide, dimethylformamide, dimethylacetamide, diethylene glycol ethyl ether, ethylene glycol ethyl ether and propylene glycol methyl ether.

The compounds which are effective solvents for glucose are 1,2,6-hexanetriol, 1,2,4-butanetriol, glycerine, tetraethylene glycol, dimethylsulfoxide, dimethylformamide and dimethylacetamide.

The compounds which are effective solvents for gluconic acid are 1,2,6-hexanetriol, 1,2,4-butanetriol, glycerine, tetraethylene glycol, dimethylsulfoxide, dimethylformamide, dimethylacetamide and diethylene glycol ethyl ether.

The compounds which are effective solvents for mannitol are 1,2,6-hexanetriol, 1,2,4-butanetriol, glycerine, tetraethylene glycol, dimethylsulfoxide, dimethylformamide, dimethylacetamide and diethylene glycol ethyl ether.

Table 2 lists a number of common compounds which will not dissolve sorbitol, xylitol, glucose, gluconic acid or mannitol.

TABLE 2

Ineffective Solvents For Sorbitol, Xylitol, Glucose, Gluconic Acid Or Mannitol

| | |
| --- | --- |
| Ethyl ether | Methy ethyl ketone |
| Acetone | 1,4-Dioxane |
| t-Butanol | Isobutanol |
| Ethanol | Diacetone alcohol |
| 1,Butoxy ethoxy-2-propanol | Isophorone |
| Diethylene glycol methyl ether | Diethylene glycol butyl ether |
| Tripropylene glycol methyl ether | Ethylene glycol hexyl ether |
| | Diethylene glycol dimethyl ether |
| Ethylenee glycol phenyl ether | Ethylene glycol butyl ether |
| Sulfolane | Acetonitrile |
| Diethylene glycol hexyl ether | 2-Nitropropane |
| Nitromethane | Adiponitrile |
| Benzonitrile | 2-Hydroxy acetphenone |
| Acetonyl acetone | n-Propanol |
| Propiophenone | n-Butanol |
| Isopropanol | |

THE USEFULNESS OF THE INVENTION

The usefulness or utility of this invention is that by using certain organic compounds as the solvent, sorbitol, xylitol, glucose, gluconic acid or mannitol can be put into a solution which has a pH close to seven (neutral), thus making these carbohydrates available to acid unstable treatment.

WORKING EXAMPLES

1. Ten grams of sorbitol and 10 grams of tetraethylene glycol were heated until the sorbitol was completely dissolved in the tetraethylene glycol. Upon cooling to 25° C., both compounds remained in a single liquid phase. The pH of the solution was 5.4.

2. Ten grams of xylitol and 10 grams of ethylene glycol ethyl ether were heated until the xylitol was completely dissolved in the ethylene glycol ethyl ether. Upon cooling to 25° C., both compounds remained in a single liquid phase. The pH of the solution was 5.9.

3. Ten grams of glucose and 10 grams of 1,2,4-butanetriol were heated until the glucose was completely dissolved in the 1,2,4-butanetriol. Upon cooling to 25° C., both compounds remained in a single liquid phase. The pH of the solution was 5.8.

4. Ten grams of gluconic acid and 10 grams of diethylene glycol ethyl ether were heated until the gluconic acid was completely dissolved in the diethylene glycol ethyl ether. Upon cooling to 25° C., both compounds remained in a single liquid phase. The pH of the solution was 5.2.

5. Ten grams of mannitol and 10 grams of dimethylacetamide were heated until the mannitol was completely dissolved in the dimethylacetamide. Upon cooling to 25° C., both compounds remained in a single liquid phase. The pH of the solution was 5.6.

I claim:

1. A method for converting mannitol into a single liquid phase having a pH in the range of 5 to 6 which consists of dissolving mannitol in dimethylacetamide.

* * * * *